(12) United States Patent
Unno et al.

(10) Patent No.: US 10,143,379 B2
(45) Date of Patent: Dec. 4, 2018

(54) FLUORESCENCE DETECTION DEVICE

(71) Applicants: NATIONAL UNIVERSITY CORPORATION HAMAMATSU UNIVERSITY SCHOOL OF MEDICINE, Hamamatsu-shi, Shizuoka (JP); HAMAMATSU PHOTONICS K.K., Hamamatsu-shi, Shizuoka (JP)

(72) Inventors: Naoki Unno, Hamamatsu (JP); Yoshimasa Hattori, Hamamatsu (JP); Mitsuharu Miwa, Hamamatsu (JP)

(73) Assignees: NATIONAL UNIVERSITY CORPORATION HAMAMATSU UNIVERSITY SCHOOL OF MEDICINE, Hamamatsu-shi, Shizuoka (JP); HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 492 days.

(21) Appl. No.: 14/378,732

(22) PCT Filed: Feb. 18, 2013

(86) PCT No.: PCT/JP2013/053862
§ 371 (c)(1),
(2) Date: Aug. 14, 2014

(87) PCT Pub. No.: WO2013/125484
PCT Pub. Date: Aug. 29, 2013

(65) Prior Publication Data
US 2015/0073273 A1 Mar. 12, 2015

(30) Foreign Application Priority Data
Feb. 20, 2012 (JP) .................................. 2012-034531

(51) Int. Cl.
*A61B 5/00* (2006.01)
*G01N 21/64* (2006.01)

(52) U.S. Cl.
CPC ............ *A61B 5/0071* (2013.01); *A61B 5/418* (2013.01); *A61B 5/6824* (2013.01);
(Continued)

(58) Field of Classification Search
None
See application file for complete search history.

(56) References Cited

U.S. PATENT DOCUMENTS 4,224,948 A 9/1980 Cramer et al.
4,291,228 A * 9/1981 Thompson .............. G01T 1/202
250/363.03
(Continued)

FOREIGN PATENT DOCUMENTS

CN 1260875 7/2000
CN 101495852 7/2009
(Continued)

OTHER PUBLICATIONS

Suzuki, M., et al., "Lymphatic function recovered after GSV stripping," Phlebology Digest, 2010, pp. 16-17.
(Continued)

*Primary Examiner* — Katherine Fernandez
*Assistant Examiner* — Bradley Impink
(74) *Attorney, Agent, or Firm* — Drinker Biddle & Reath LLP (57) ABSTRACT

A fluorescence detection device comprises: a plurality of light sources that apply an excitation light from an outside of a living body toward fluorescent dye previously injected into the living body; and a plurality of detectors that detect fluorescence emitted from the fluorescent dye by the excitation light, and output the detected fluorescence as an
(Continued)

electric signal. The plurality of light sources and the plurality of detectors are arranged in at least one line. At least one detector is placed between two light sources, and at least one light source is placed between two detectors.

6 Claims, 12 Drawing Sheets

(52) U.S. Cl.
CPC .......... *A61B 5/6828* (2013.01); *A61B 5/6831* (2013.01); *G01N 21/645* (2013.01); *A61B 2562/0242* (2013.01); *A61B 2562/043* (2013.01); *A61B 2562/046* (2013.01)

(56) References Cited

U.S. PATENT DOCUMENTS

| | | | |
|---|---|---|---|
| 2002/0045805 A1* | 4/2002 | Gopinathan | A61B 5/0002 600/300 |
| 2004/0152976 A1* | 8/2004 | Hengerer | A61B 5/0091 600/431 |
| 2009/0054908 A1 | 2/2009 | Zand et al. | |
| 2010/0056934 A1* | 3/2010 | Cho | A61B 5/02416 600/502 |
| 2010/0100160 A1* | 4/2010 | Edman | A61B 5/0059 607/88 |

FOREIGN PATENT DOCUMENTS

| | | |
|---|---|---|
| JP | H10-127612 A | 5/1998 |
| JP | 2002-502652 | 1/2002 |
| JP | 2002-360530 A | 12/2002 |
| JP | 2004-525684 A | 8/2004 |
| JP | 2004-344668 | 12/2004 |
| JP | 2006-271896 | 10/2006 |
| JP | 2008-220926 A | 9/2008 |
| JP | 2010-051790 A | 3/2010 |
| JP | 2010-220638 A | 10/2010 |
| WO | WO 2008/114398 | 9/2008 |
| WO | WO-2010/137358 A1 | 12/2010 |
| WO | WO 2010/150751 | 12/2010 |

OTHER PUBLICATIONS

Minoru Suzuki, MD, et al., "Impaired lymphatic function recovered after great saphenous vein stripping in patients with varicose vein: Venodynamic and lymphodynamic results," Journal of Vascular Surgery, vol. 50, No. 5, 2009, pp. 1085-1091.

Naoki Unno, et al., "A novel method of measuring human lymphatic pumping using indocyanine green fluorescence lymphography," Japanese Journal of Lymphology, 2010, pp. 87-90, including English language translation.

N. Unno, et al., Influence of Age and Gender on Human Lymphatic Pumping Pressure in the Leg, Lymphology 44, 2011, pp. 113-120.

Naoki Unno, MD, et al., "A novel method of measuring human lymphatic pumping using indocyanine green fluorescence lymphography," Journal of Vascular Surgery, Oct. 2010, pp. 946-952.

N. Unno, et al., "Quantitative Lymph Imaging for Assessment of Lymph Function using Indocyanine Green Fluorescence Lymphography," Eur J Vasc Endovasc Surg, 36, 2008, pp. 230-236.

* cited by examiner

FLUORESCENCE DETECTION DEVICE

TECHNICAL FIELD

An aspect of the present invention relates to a device and a method for detecting fluorescence emitted from fluorescent dye injected into a living body.

BACKGROUND ART

A method for capturing a position and movement of fluorescent dye injected into a living body includes a technique for taking and generating an image of fluorescence using an infrared camera. For example, Patent Literature 1 mentioned below describes a method for taking and generating an image of fluorescent dye injected into lymph vessels.

CITATION LIST

Patent Literature

Patent Literature 1: WO 2010/137358

SUMMARY OF INVENTION

Technical Problem

Although an image of fluorescent dye can be easily obtained by taking an image thereof using an infrared camera, a camera view is limited to limit a range of single observation. For example, when the infrared camera is used, single observation of a 360° range of lymph flows flowing through an extremity is difficult. Also, when the infrared camera is used, an observer of the taken image requires some experience. Thus, it is demanded to easily and accurately capture fluorescent dye in a living body.

Solution to Problem

An aspect of the present invention provides a fluorescence detection device comprising: a plurality of light sources that apply an excitation light from an outside of a living body toward fluorescent dye previously injected into the living body; and a plurality of detectors that detect fluorescence emitted from the fluorescent dye by the excitation light, and output the detected fluorescence as an electric signal, wherein the plurality of light sources and the plurality of detectors are arranged in at least one line, at least one detector is placed between two light sources, and at least one light source is placed between two detectors.

According to the aspect, the plurality of light sources and detectors are arranged in at least one line so that the detector exists between the two light sources and the light source exists between the two detectors. Such an arrangement allows fluorescence to be detected at substantially the same area as where the excitation light is emitted, thereby allowing a position of the fluorescent dye to be accurately captured. Since the detected fluorescence is output as an electric signal, the fluorescent dye can be easily captured without relying on observer's vision.

In the fluorescence detection device according to another aspect, the light sources and the detectors may be alternately arranged. The light sources and the detectors are arranged in this manner, thereby expanding an application range of the excitation light along the line and allowing the position of the fluorescent dye to be accurately captured.

In the fluorescence detection device according to a further aspect, amplifiers may be individually connected to the detectors, and an electric signal from each amplifier may be individually output as a signal from the fluorescence detection device. In this case, the signal from the amplifier corresponds to a position of the detector, thereby allowing a detector having detected fluorescence to be identified. This allows the position of the fluorescent dye in the living body to be more specifically identified.

In the fluorescence detection device according to a further aspect, amplifiers may be individually connected to groups including a predetermined number of detectors continuously arranged, and an electric signal from each amplifier may be individually output as a signal from the fluorescence detection device. In this case, the signal from the amplifier corresponds to a rough position of a detector that has detected fluorescence, thereby allowing a rough position of the fluorescent dye in the living body to be identified. Also, reducing the number of amplifiers can reduce manufacturing cost of the fluorescence detection device.

In the fluorescence detection device according to a further aspect, one amplifier may be connected to all the detectors, and an electric signal from the amplifier may be output as a signal from the fluorescence detection device. In this case, one amplifier may be prepared, thereby facilitating fabrication of the fluorescence detection device, and reducing manufacturing cost.

The fluorescence detection device according to a further aspect may further comprise a band to be wrapped around a human arm or leg, and the plurality of light sources and the plurality of detectors may be arranged in a longitudinal direction of the band. This allows the position of the fluorescent dye injected into a human extremity to be easily and accurately captured. Also, the band allows the fluorescence detection device to be easily fitted on the extremity.

The fluorescence detection device according to a further aspect may further comprise a support portion provided on a surface on which the plurality of light sources and the plurality of detectors are arranged, for ensuring a predetermined clearance between the light sources and the detectors and skin of a subject. The support portion expands an application range of the excitation light, thereby ensuring excitation of fluorescent dye with a wide range.

Advantageous Effects of Invention

According to one aspect of the present invention, fluorescent dye in a living body can be easily and accurately captured.

BRIEF DESCRIPTION OF DRAWINGS

FIGS. 2(*a*) to 2(*c*) are partial plan views of the detection band showing an example of arrangement of light sources and detectors.

DESCRIPTION OF EMBODIMENTS

Now, an embodiment of the present invention will be described in detail with reference to the accompanying drawings. In descriptions of the drawings, the same or equivalent components are denoted by the same reference numerals, and overlapping descriptions will be omitted.

First, with reference to FIGS. 1 to 6, a configuration of a fluorescence detection band (fluorescence detection device; hereinafter simply referred to "detection band") 10 according to the embodiment will be described. The detection band 10 is a device that applies an excitation light to fluorescent dye injected into a living body, detects fluorescence emitted from the fluorescent dye by the excitation light, and outputs the detection as an electric signal. The detection band 10 is intended to measure a lymph flow in a human extremity. The detection band 10 includes a plurality of light sources 11, a plurality of detectors 12, and amplifiers 13 that amplify electric signals output from the detectors 12. A pair of hook and loop fasteners 15 are provided on opposite ends of the detection band 10, and the detection band 10 is secured to an arm or a leg by the hook and loop fasteners 15. Each light source 11 is connected to an external light source drive 20, and each detector 12 is connected to an output terminal (not shown). Conductive wires are included in a cable 14.

An example of fluorescent dye detected by the detection band 10 is indocyanine green (ICG). The ICG is an agent approved in Japan, having very few side effects, and routinely used in general hospitals. The ICG is very inexpensive and easy to handle. As the fluorescent dye, substances such as fluorescent dextran may be used other than the ICG.

The light source 11 is an instrument that emits an excitation light having a predetermined wavelength that can excite the fluorescent dye injected into the living body. Each light source 11 continuously emits excitation lights with electric power supplied from the light source drive 20. The wavelength of the excitation light is set depending on the fluorescent dye, and if the fluorescent dye is, for example, ICG, the wavelength of the excitation light is 700 to 810 nm. The light source 11 may be a light emitting diode (LED) or a laser diode (LD).

The detector 12 is an instrument that detects fluorescence emitted from the fluorescent dye by the excitation light from the light source 11, and outputs intensity of the detected fluorescence as an electric signal. The detector 12 includes a photodiode (PD), and a filter through which only a light having a longer wavelength than the excitation light passes. The filter is used to block the excitation light or an external light and efficiently detect fluorescence, and is selected depending on a wavelength of fluorescence to be detected. For example, if the fluorescent dye is ICG, a filter is used through which only a light having a longer wavelength than 810 nm passes.

Figure 1:
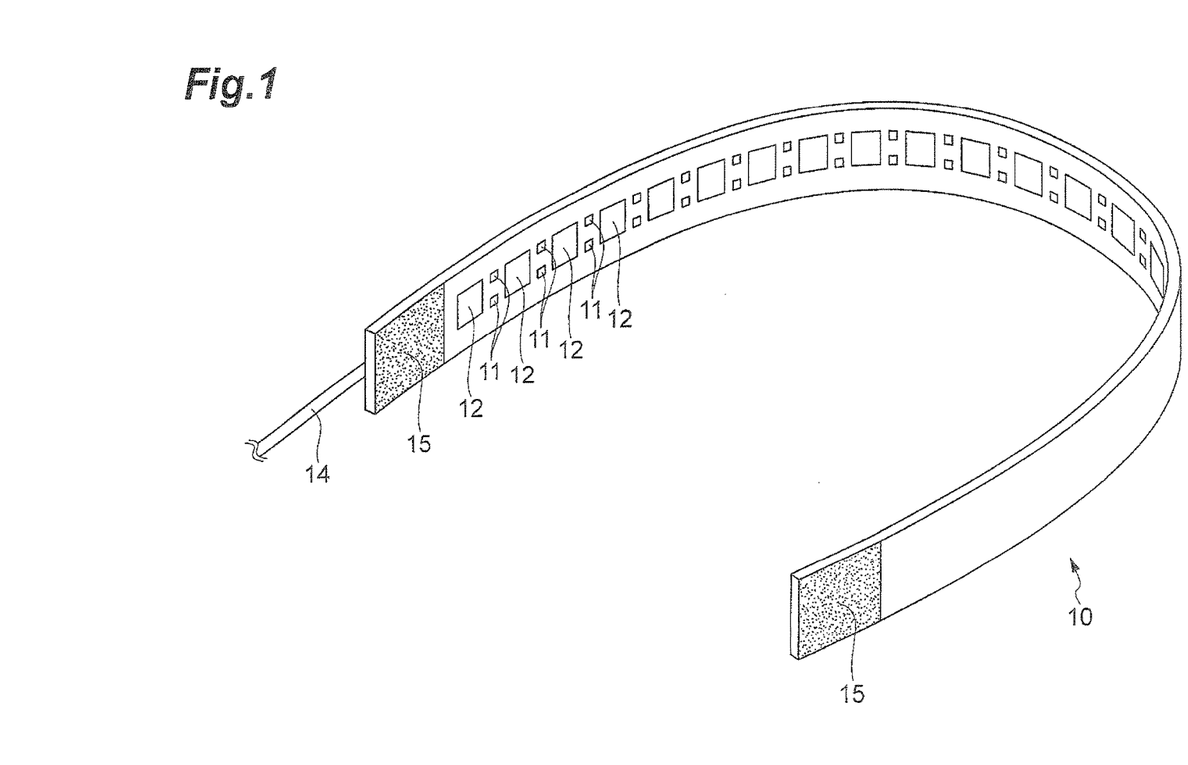
FIG. 1 is a perspective view of a fluorescence detection band (detection band) according to an embodiment.

As shown in FIG. 1, the plurality of light sources 11 and detectors 12 are arranged in one line in a longitudinal direction of the detection band 10 on an inner side (a side facing subject's skin) of the detection band 10. At least one detector 12 is placed between two light sources 11 continuously arranged, and least one light source 11 is placed between two detectors 12 continuously arranged, but a specific placement method thereof is not limited.

Figure 2:
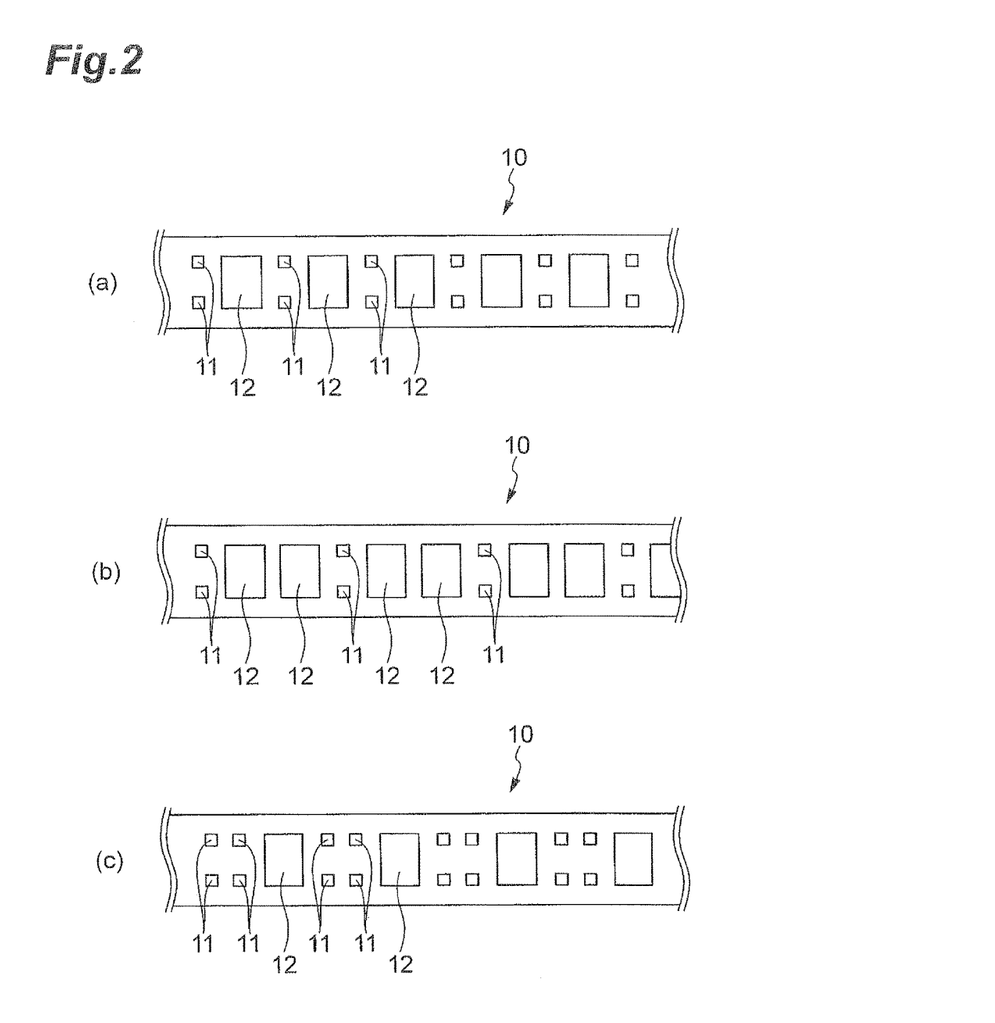

FIG. 2 shows an example of the placement method. In FIG. 2, in view of an amount of excitation light (amount of light) emitted from one light source 11, two light sources 11 arranged in a width direction of the detection band 10 are a set of light sources 11. For example, as shown in FIG. 2(a), the light sources 11 and the detectors 12 may be alternately placed. Alternatively, as shown in FIG. 2(b), a plurality of (for example, two) detectors 12 may be placed between two sets of light sources 11 next to each other. Alternatively, as shown in FIG. 2(c), plural sets (for example, two sets) of light sources 11 may be placed between two detectors 12 next to each other. Arranging the plurality of light sources 11 in the width direction of the detection band 10, which is as shown in FIG. 2, is not essential, and only one light source 11 may be placed in one spot.

For the mechanism that outputs the detected fluorescence as an electric signal, Patent Literature 1 mentioned above describes a detector having a line sensor and a line LED, however, it is to be noted that the structure of the detection band 10 is completely different from the detector in Patent Literature 1.

As such, how the light sources 11 and the detectors 12 are arranged in the longitudinal direction of the detection band 10 may be optionally determined, and in any case, when the detection band 10 is fitted on the extremity, the light sources 11 and the detectors 12 surround a 360° range of the fitted area.

Figure 3:
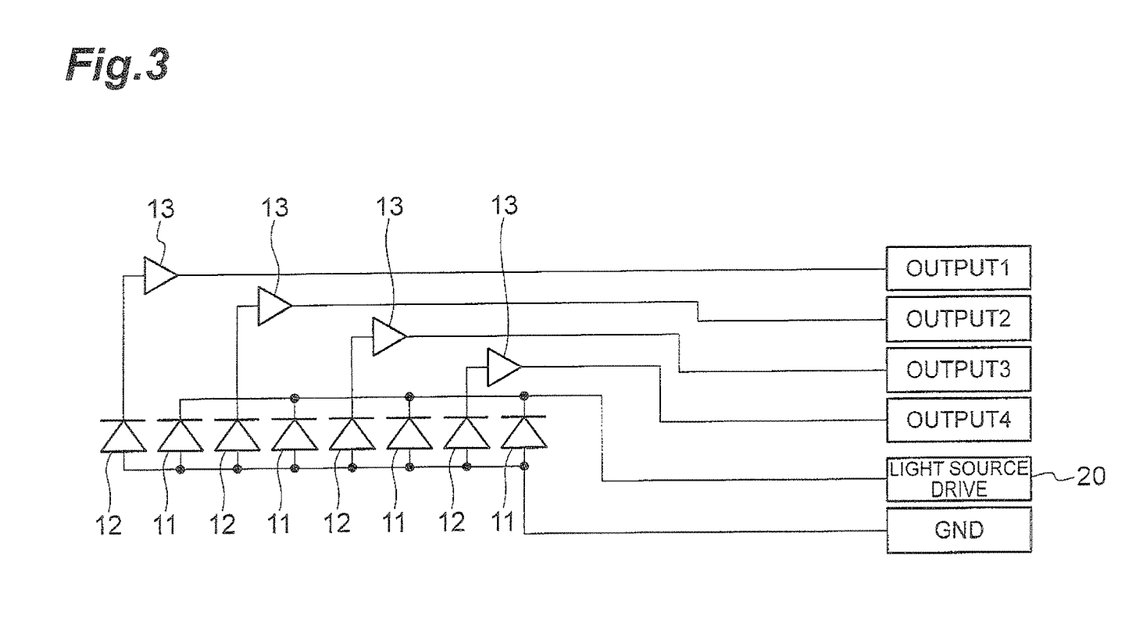
FIG. 3 is a circuit view of an aspect of the detection band in FIG. 1.
Figure 4:
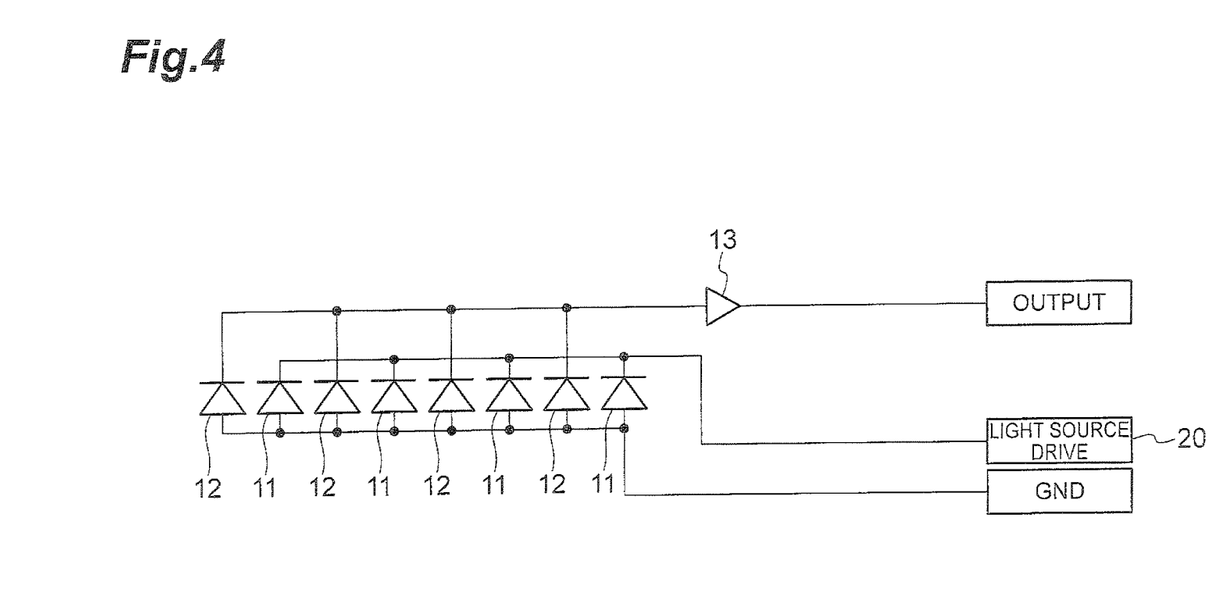
FIG. 4 is a circuit view of another aspect of the detection band in FIG. 1.
Figure 5:
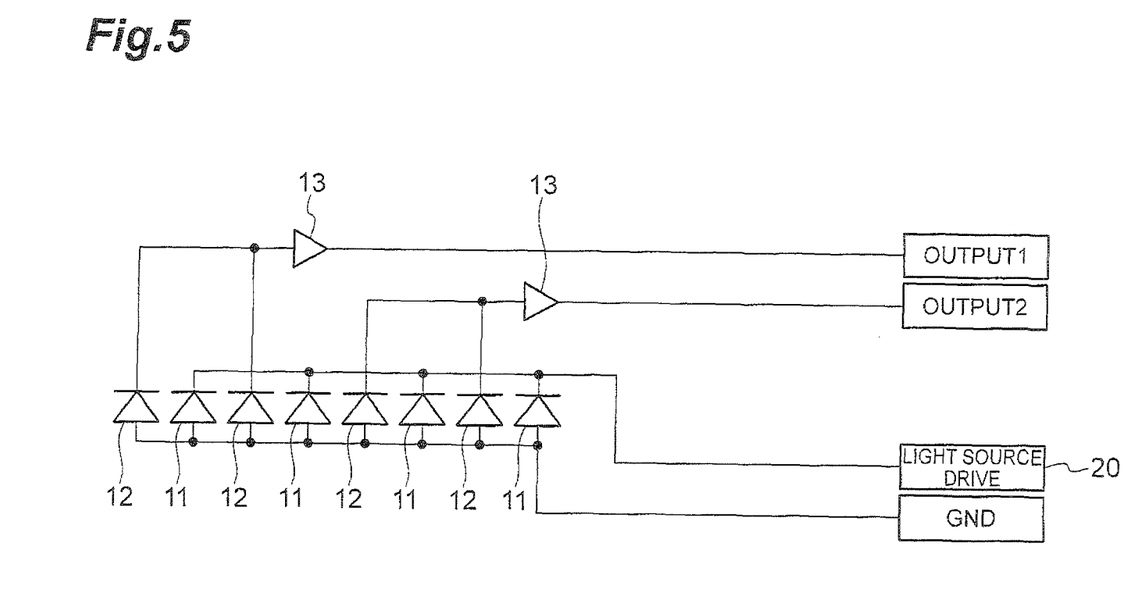
FIG. 5 is a circuit view of a further aspect of the detection band in FIG. 1.

The amplifier 13 is an instrument that is connected to the detector 12, amplifies an electric signal from the detector 12, and outputs the electric signal to a measurement device such as a fluorescence intensity meter. A connection method of the amplifier 13 is not limited. For example, as shown in FIG. 3, an amplifier 13 may be connected to each detector 12 (serial connection), and as shown in FIG. 4, all detectors 12 may be connected to one amplifier 13 (parallel connection). Alternatively, as shown in FIG. 5, several detector 12 continuously arranged may be connected to one amplifier (grouping of detectors).

For the serial connection, the signal from the amplifier 13 corresponds to the position of the detector 12, thereby allowing the detector 12 having detected fluorescence to be identified. This allows the position of the fluorescent dye in the living body to be more specifically identified. Using the parallel connection can facilitate fabrication of the detection band 10, and reduce manufacturing cost. In grouping the detectors, advantages of both the serial connection and the parallel connection can be obtained to some extent.

Figure 6:
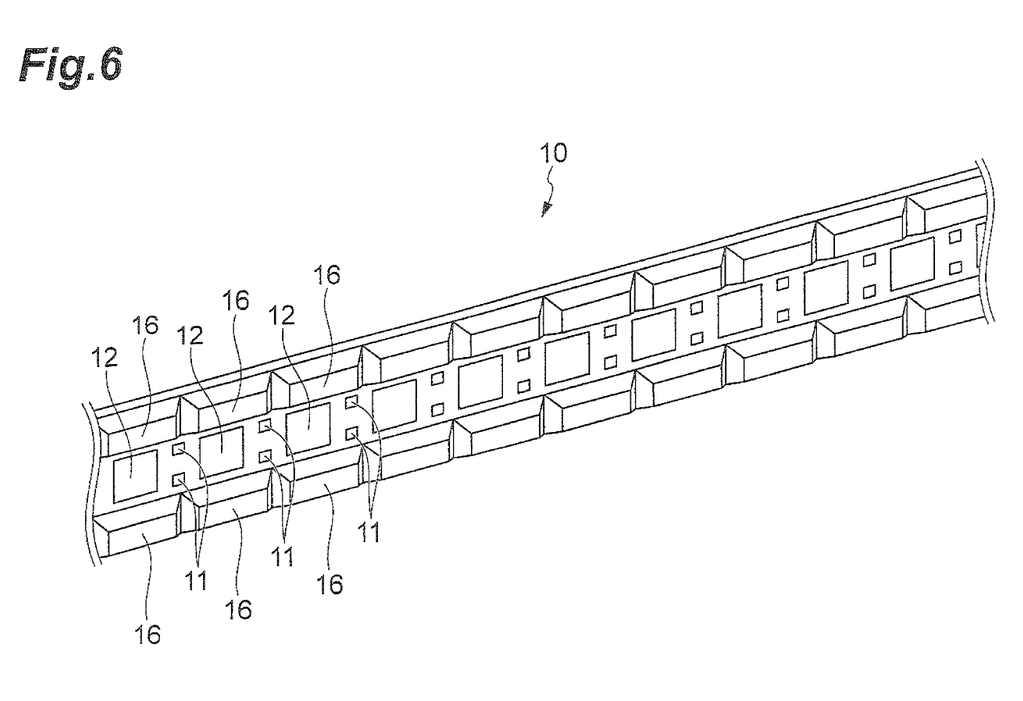
FIG. 6 is a partial perspective view of a detection band including a support portion.

As shown in FIG. 6, on the inner side of the detection band 10, support portions 16 may be provided for ensuring a predetermined clearance between each light source 11 and each detector 12 and the subject's skin in use. The support portions 16 are provided at opposite ends in the width direction of the detection band 10, and extend in the longitudinal direction of the detection band 10. The support portions 16 expand an application range of the excitation light, thereby eliminating a dead region between the light sources 11 and ensuring excitation of fluorescent dye in a wide range. On the other hand, without the support portions 16 as in FIG. 1, the excitation light can reach a deep part in the living body, thereby ensuring excitation of fluorescent dye in a deep position.

Figure 7:
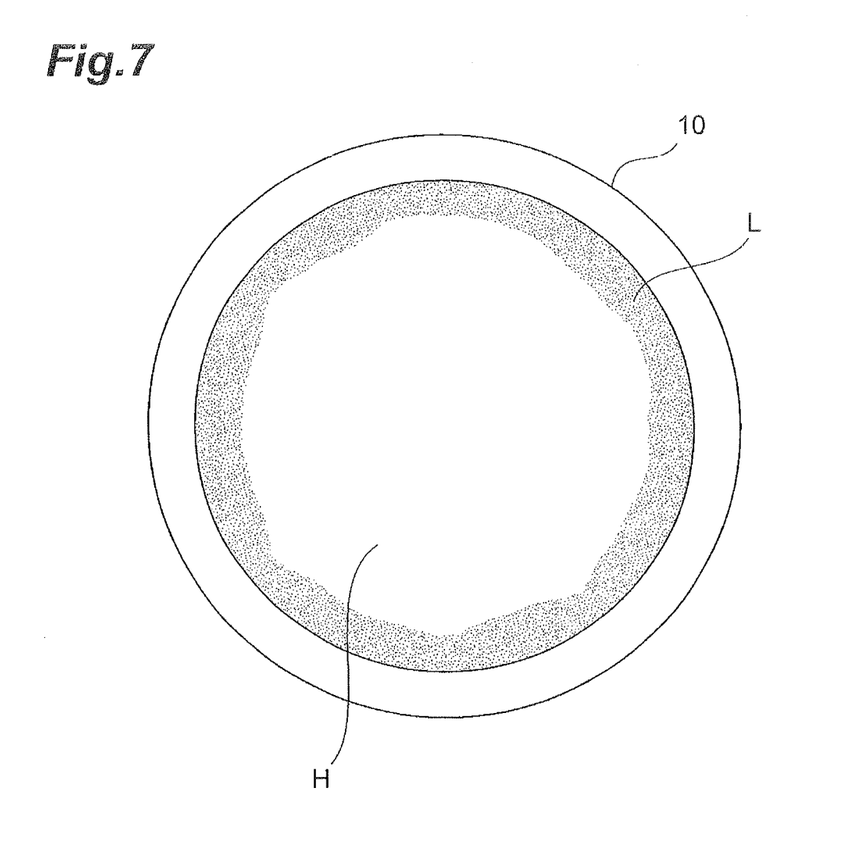
FIG. 7 is a schematic view of a range of reach of light from the detection band in FIG. 6.
Figure 8:
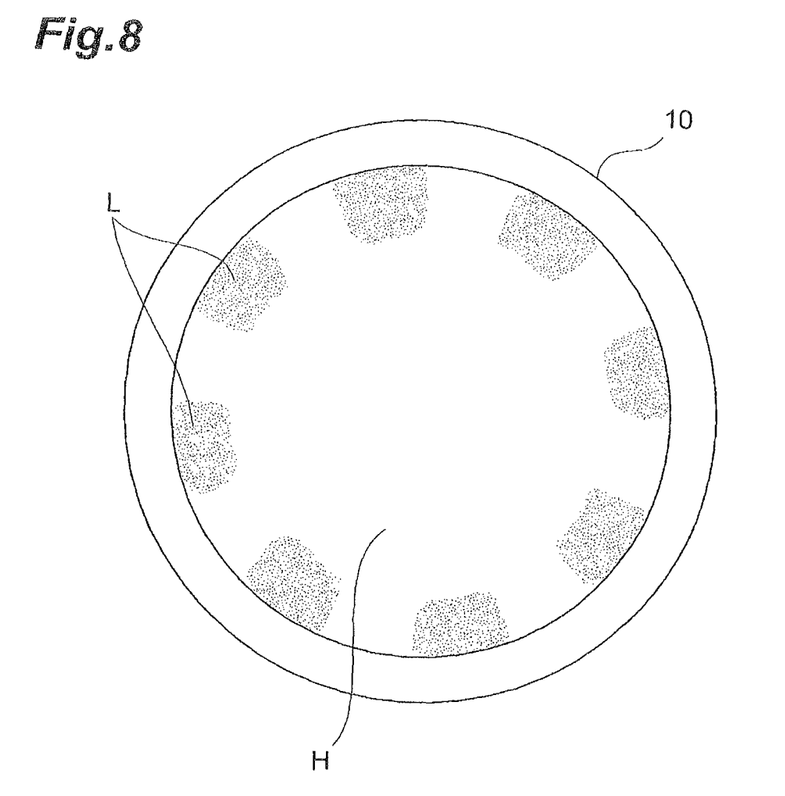
FIG. 8 is a schematic view of a range of reach of light from the detection band in FIG. 1.

FIGS. 7 and 8 show a difference in reach of the light sources. FIGS. 7 and 8 show a light L penetrating into a phantom H when the detection band 10 is wrapped around the phantom H simulating an extremity and the light sources are lit. FIG. 7 shows penetration of the light L with the support portions, and FIG. 8 shows penetration of the light L without the support portions. As shown in FIG. 7, with the support portion, the light L spreads over a 360° range, which means that there is no dead area. On the other hand, without the support portions as shown in FIG. 8, the light L reaches to a deeper part than the case in FIG. 7.

Figure 9:
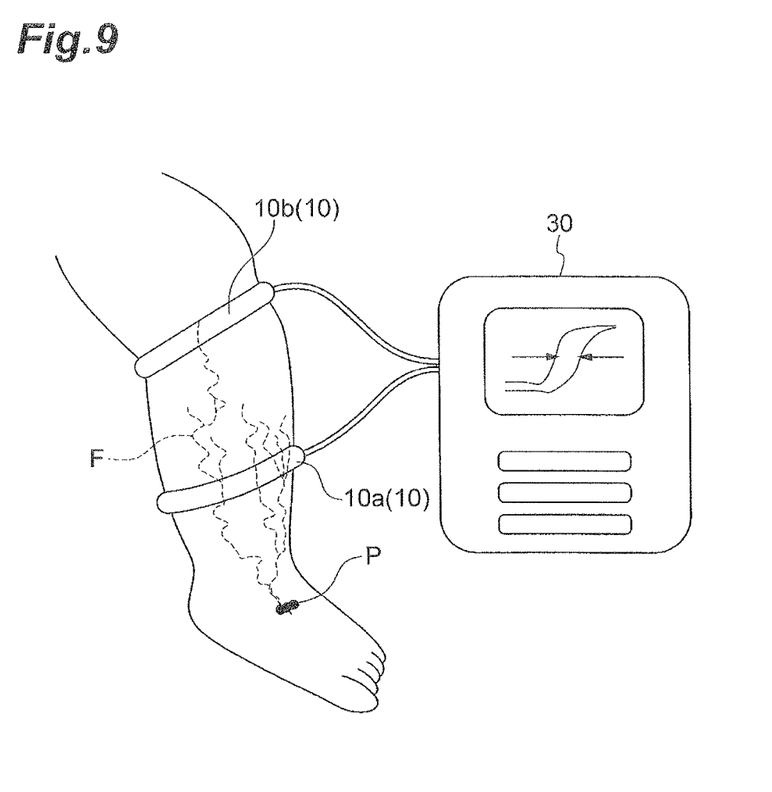
FIG. 9 is a conceptual view of a system that measures a lymph flow rate.

Next, an example of use of the detection band 10 will be described. FIG. 9 shows an example of measurement of a lymph flow rate. In this case, two detection bands 10 and a fluorescence intensity meter 30 including the light source drive 20 are prepared. Two detection bands 10 are fitted at a predetermined interval on one extremity. Hereinafter, the detection band 10 fitted closer to an injection point P of fluorescent dye is referred to as "a first band 10a", and the detection band 10 farther from the injection point is referred to as "a second band 10b". It can be also said that the first band 10a is a detection band on a peripheral side, and the second band 10b is a detection band on a central side. The first and second detection bands 10a, 10b are both connected to the fluorescence intensity meter 30.

The fluorescence intensity meter 30 is a device that indicates intensity of fluorescence at fitting areas of the first and second bands 10a, 10b based on signals input from the bands. Thus, a measurer can visually see movement of the fluorescent dye. The fluorescence intensity meter also has a timing function based on the input signals. The fluorescence intensity meter 30 may determine passage of the fluorescent dye based on magnitude of changes of fluorescence intensity, or determine that the fluorescent dye has passed when the detected intensity reaches a threshold or more previously stored therein. Of course, a specific determination method is not limited thereto.

A procedure for measuring the lymph flow rate is as described below. First, the first and second bands 10a, 10b are fitted on a subject's extremity, and light sources 11 on the detection bands are lit. Then, fluorescent dye F such as ICG is injected into a lymph vessel at an area on a more peripheral side than the first band 10a (the injection point P in FIG. 9). The injected fluorescent dye starts moving from the injection point P through the lymph vessel to the center of the body, and then reaches the fitting area of the first band 10a. At this time, the fluorescent dye F receives the excitation light from the light source 11 on the first band 10a to emit fluorescence, and the detector 12 on the band 10a detects the fluorescence. When a signal from the detector 12 is output to the fluorescence intensity meter 30, the fluorescence intensity meter 30 starts timing.

The fluorescent dye F then continues moving toward the center, and at least a part of the fluorescent dye F reaches the fitting area of the second band 10b. The fluorescent dye F receives the excitation light from the light source 11 on the second band 10b to emit fluorescence, and the detector 12 on the band 10b detects the fluorescence. When the signal from the detector 12 is output to the fluorescence intensity meter 30, the fluorescence intensity meter 30 finishes timing, thereby obtaining time for the fluorescent dye to move from the first band 10a to the second band 10b. Since a distance between the two bands is known, the lymph flow rate is obtained from the distance and the obtained time.

Figure 10:
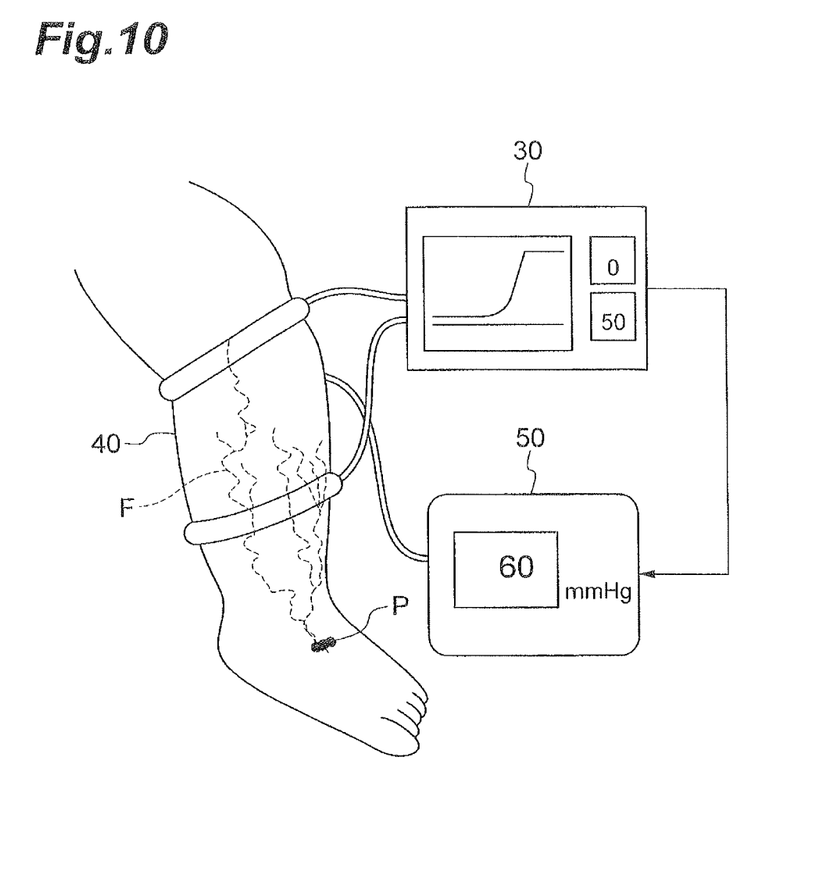
FIG. 10 is a conceptual view of a system that measures lymphatic pressure.

Next, an example of measurement of lymphatic pressure will be described. As shown in FIG. 10, in this case, a manchette (pressure band) 40 having a function corresponding to the detection band 10, a fluorescence intensity meter 30 including a light source drive, and a manometer 50 that operates simultaneously with the fluorescence intensity meter 30 are prepared.

Figure 11:
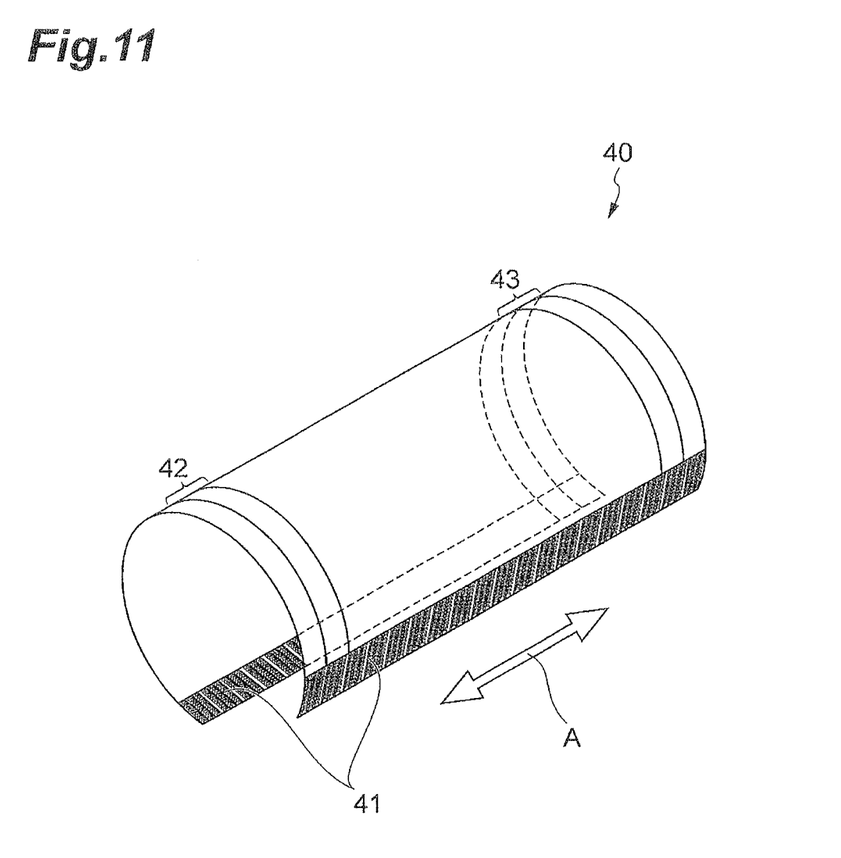
FIG. 11 is a schematic view of a manchette used in the system in FIG. 8.

The manchette 40 is fitted to surround a part of a human arm or leg. The manchette 40 includes an air bag, and the manometer 50 supplies air into the air bag to pressurize the covered area (vital observation portion). As shown in FIG. 11, the manchette 40 has a band shape, and is secured to the arm or leg by a pair of hook and loop fasteners 41 provided on opposite edges extending in an insertion direction (arrow A in FIG. 11) of the arm or leg. Detection portions having a structure corresponding to that of the detection band 10 are provided on opposite edges in a width direction of the manchette 40. Hereinafter, a detection portion closer to an injection point of fluorescent dye (detection portion on a peripheral side) when the manchette 40 is fitted is a first detection portion 42, and a detection portion farther from the injection point (detection portion on a central side) is a second detection portion 43. When the manchette 40 is wrapped around the arm or leg, the first detection portion 42 and the second detection portion 43 surround the arm or leg similarly to the detection band 10.

The fluorescence intensity meter 30 is a device that indicates intensity of fluorescence at the first and second detection portions 42, 43 based on signals input from the first and second detection portions 42, 43. Also, the fluorescence intensity meter 30 outputs a passage signal that indicates that the fluorescent dye has first passed through each of two areas surrounded by the first and second detection portions 42, 43 to the manometer 50 at the time of the passage. Specifically, the fluorescence intensity meter 30 outputs a first passage signal to the manometer 50 when obtaining a first input signal from the first detection portion 42, and outputs a second passage signal to the manometer 50 when obtaining a first input signal from the second detection portion 42 in one measurement. Thus, two passage signals are output from the fluorescence intensity meter 30 in one measurement. The first passage signal means that the fluorescent dye has passed below the first detection portion 42. On the other hand, the second passage signal means that the fluorescent dye has moved through the area covered by the manchette 40, and passed below the second detection portion 43.

The manometer 50 is a device that measures pressure of the manchette 40. The manometer 50 is connected to the manchette 40 via a pipe for feeding or sucking air to or from the manchette 40, and electrically connected to the fluorescence intensity meter 30.

The manometer 50 starts feeding air into the air bag in the manchette 40 when the first passage signal is input from the fluorescence intensity meter 30, and pressurizes the manchette 40 so as to block the lymph flow in the vital observation portion (for example, 100 mmHg). Then, the manometer 50 reduces the pressure of the manchette 40 in increments of a predetermined amount (for example, in increments of 5 mmHg) at predetermined timing until the second passage signal is input. Then, when the second passage signal is input, the manometer 50 records the pressure of the manchette 40 at that time as lymphatic pressure, and outputs the lymphatic pressure via a monitor or the like.

A procedure for measuring the lymphatic pressure is as described below. First, the manchette 40 is fitted on the extremity, and the light sources 11 on the two detection portions are lit. Then, fluorescent dye F such as ICG is injected into a lymph vessel at an area on a more peripheral side than the manchette 40 (the injection point P in FIG. 10).

The injected fluorescent dye starts moving from the injection point P through the lymph vessel to the center of the body. Then, when the fluorescent dye F reaches the first detection portion 42, the fluorescent dye F receives the excitation light from the light source 11 on the first detection portion 42 to emit fluorescence, and the detector 12 on the first detection portion 42 detects the fluorescence.

In accordance with the detection, the fluorescence intensity meter 30 determines that the fluorescent dye has passed below the first detection portion 42, and in accordance with the determination, the manometer 50 pressurizes the manchette 40 to block a lymph flow in the fitting area of the manchette 40. Then, the manometer 50 continues pressure measurement while gradually reducing the pressure of the manchette 40. Then, when the pressure reduction causes autonomous contractility of the lymph vessel to exceed the pressure of the manchette 40, the fluorescent dye F starts moving toward the center (restart of the lymph flow), and at least a part of the fluorescent dye F reaches the second detection portion 43. At this time, the fluorescent dye F receives the excitation light from the light source 11 on the second detection portion 43 to emit fluorescence, and the detector 12 on the second detection portion 43 detects the fluorescence.

In accordance with the detection, the fluorescence intensity meter 30 determines that the fluorescent dye has passed below the second detection portion 43, and in accordance with the determination, the manometer 50 measures the pressure of the manchette 40 at that time as lymphatic pressure, and displays measurement results.

As described above, according to this embodiment, the plurality of light sources 11 and detectors 12 are arranged in one line so that the detector 12 exists between the two light sources 11 and the light source 11 exists between the two detectors 12, thereby allowing fluorescence to be detected at substantially the same area as where the excitation light is emitted. This allows the position of the fluorescent dye to be accurately captured. Also, since the detected fluorescence is output as the electric signal, the fluorescent dye can be easily captured without relying on observer's vision.

The present invention has been described above in detail based on the embodiment. However, the present invention is not limited to the embodiments. The present invention may be changed in various manners without departing from the gist thereof.

In the example of use described with reference to FIGS. 9 to 11, the fluorescence detection device detects the fluorescent dye injected into the lymph vessel, but the fluorescence detection device may detect the fluorescent dye injected into other areas (for example, cancer cell or a particular organ).

Figure 12:
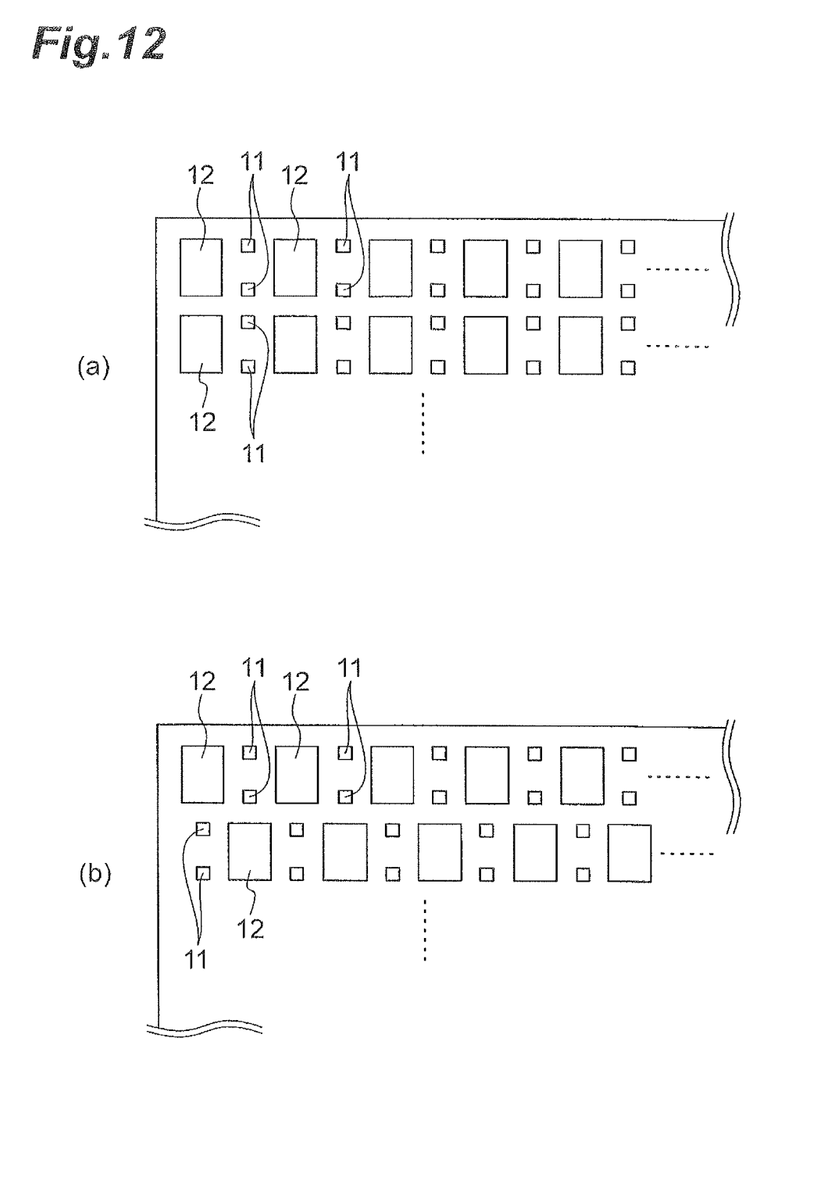
FIGS. 12(a) and 12(b) are plan views of a fluorescence detection device showing an example of arrangement of light sources and detectors according to a variant.

In the above described embodiment, the plurality of light sources 11 and the plurality of detectors 12 are arranged in one line, but the present invention may be applied to a fluorescence detection device in which light sources 11 and detectors 12 are two-dimensionally arranged. For example, a fluorescence detection device in which a plurality of light sources 11 and a plurality of detectors 12 are arranged in each horizontal row as shown in FIG. 12(a), or a fluorescence detection device in which a plurality of light sources 11 and a plurality of detectors 12 are arranged in each horizontal row and each vertical column as shown in FIG. 12(b) also fall within the scope of the present invention. If the fluorescence detection device shown in FIG. 12 has a shape like the manchette shown in FIG. 11, for example, a three-dimensional map of lymph vessels may be generated.

The fluorescence detection device may have a shape other than the band shape. For example, the present invention may be applied to a fluorescence detection device formed to cover only a part of human chest or abdomen.

REFERENCE SIGNS LIST

10, 10*a*, 10*b* . . . detection band (fluorescence detection device), 11 . . . light source, 12 . . . detector, 13 . . . amplifier, 14 . . . cable, 15 . . . hook and loop fastener, 16 . . . support portion, 20 . . . light source drive, 30 . . . fluorescence intensity meter, 40 . . . manchette, 41 hook and loop fastener, 42 . . . first detection portion (fluorescence detection device), 43 . . . second detection portion (fluorescence detection device), 50 . . . manometer

The invention claimed is:

1. A fluorescence detection device comprising:
   a plurality of light sources configured to apply an excitation light from an outside of a living body toward fluorescent dye previously injected into the living body;
   a plurality of detectors configured to detect fluorescence emitted from the fluorescent dye by the excitation light, and output the detected fluorescence as an electric signal;
   a band including a surface on which the plurality of light sources and the plurality of detectors are arranged in a longitudinal direction of the band, wherein the surface of the band is adapted to fit around an extremity of the living body and the plurality of light sources and the plurality of detectors are arranged on the band to surround a 360 degree range of the fitted surface; and
   a plurality of support portions provided on the surface and configured to ensure a predetermined clearance between the surface and skin of a subject,
   wherein the plurality of support portions is configured to be provided at opposite ends in a width direction of the band and extending in the longitudinal direction of the band, such that the plurality of support portions is disposed along the outside of the band.

2. The fluorescence detection device according to claim 1, wherein the plurality of light sources and the plurality of detectors are alternately arranged.

3. The fluorescence detection device according to claim 1, wherein amplifiers are individually connected to the plurality of detectors, and
   an electric signal from each amplifier is individually output as a signal from the fluorescence detection device.

4. The fluorescence detection device according to claim 1, wherein amplifiers are individually connected to groups including a predetermined number of the plurality of detectors continuously arranged, and
   an electric signal from each amplifier is individually output as a signal from the fluorescence detection device.

5. The fluorescence detection device according to claim 1, wherein one amplifier is connected to all the plurality of detectors, and
   an electric signal from the amplifier is output as a signal from the fluorescence detection device.

6. The fluorescence detection device according to claim 1, wherein the band is adapted to fit around a human arm or leg.

* * * * *